US011083762B2

(12) United States Patent
Pan et al.

(10) Patent No.: US 11,083,762 B2
(45) Date of Patent: Aug. 10, 2021

(54) APPLICATION FOR WATER EXTRACT OF PLANT OF *GRACILARIACEAE* OR FERMENT THEREOF AND PHARMACEUTICAL COMPOSITION AND/OR HEALTH FOOD FOR TREATING AND/OR ALLEVIATING NERVOUS DISEASES

(71) Applicant: Industrial Technology Research Institute, Hsinchu (TW)

(72) Inventors: I-Hong Pan, Zhubei (TW); Wei-Hsuan Hsu, New Taipei (TW); Chu-Hsun Lu, Kaohsiung (TW); Shu-Fang Wen, Baoshan Township (TW); Hsin-Chieh Wu, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 570 days.

(21) Appl. No.: 15/845,394

(22) Filed: Dec. 18, 2017

(65) Prior Publication Data
US 2019/0183949 A1   Jun. 20, 2019

(51) Int. Cl.
*A61K 36/04* (2006.01)
*A61K 35/744* (2015.01)
*A61K 8/9789* (2017.01)
*A61Q 19/08* (2006.01)
*A61K 35/747* (2015.01)
*A23L 33/105* (2016.01)
*A23L 33/00* (2016.01)
*A61P 25/28* (2006.01)
*A61P 25/22* (2006.01)
*A61P 25/24* (2006.01)
*A61K 35/00* (2006.01)

(52) U.S. Cl.
CPC ............. *A61K 36/04* (2013.01); *A23L 33/00* (2016.08); *A23L 33/105* (2016.08); *A61K 8/9789* (2017.08); *A61K 35/744* (2013.01); *A61K 35/747* (2013.01); *A61P 25/22* (2018.01); *A61P 25/24* (2018.01); *A61P 25/28* (2018.01); *A61Q 19/08* (2013.01); *A61K 2035/115* (2013.01); *A61K 2236/00* (2013.01); *A61K 2236/19* (2013.01)

(58) Field of Classification Search
None
See application file for complete search history.

(56) References Cited

U.S. PATENT DOCUMENTS 9,480,864 B2   11/2016   Chavan et al.
9,526,267 B2   12/2016   Anderson et al.
2008/0226740 A1   9/2008   Chen et al.

FOREIGN PATENT DOCUMENTS

| CN | 103740780 A | 4/2014 |
|---|---|---|
| CN | 105851228 A | 8/2016 |
| JP | 2002-125587 A | 5/2002 |
| JP | 2011-105868 A | 6/2011 |
| KR | 10-2014-0096972 A | 8/2014 |
| TW | 200836755 A | 9/2008 |
| TW | I458486 B | 11/2014 |
| TW | I492766 B | 7/2015 |
| TW | I579381 B | 4/2017 |

OTHER PUBLICATIONS

Souza, et al., J. Appl. Phycol., 28:1997. (Year: 2016).*
Japanese Office Action for Appl. No. 2018-235522 dated Oct. 8, 2019.
Menteiro, V.S., et al, "Involvement of the GABAergic system in the anxiolytic effect of sulfated polysaccharides from the red seaweed *Gracilaria cornea*," J. Appl. Phycol., 2016, vol. 28, pp. 1997-2004.
Cryan et al., "Mind-altering microorganisms: the impact of the gut microbiota on brain and behaviour", Nat. Rev. Neurosci., Oct. 2012, vol. 13, pp. 701-712.
Foster et al., "Gut-brain axis: how the microbiome influences anxiety and depression", Trends Neurosci. May 2013, vol. 36, No. 5, pp. 305-312.
Goehler et al., "Campylobacter jejuni infection increases anxiety-like behavior in the holeboard: possible anatomical substrates for viscerosensory modulation of exploratory behavior", Brain Behav. Immun., Mar. 2008, vol. 22, No. 3, pp. 354-366.
Kumar et al., "Bioethanol production from *Gracilaria verrucosa*, a red alga, in a biorefinery approach", Bioresource Technol., 2013, vol. 135, pp. 150-156.
Natarajan et al., "Cholinesterase inhibitors from *Sargassum* and *Gracilaria gracilis*: seaweeds inhabiting South Indian coastal areas (Hare Island, Gulf of Mannar)", Nat. Prod. Res., 2009, vol. 23, pp. 355-369.
Prenderville et al., "Adding fuel to the fire: the impact of stress on the ageing brain", Trends in Neurosci., Jan. 2015, vol. 38, No. 1, pp. 13-25.
Ratanaburee et al., "Enhancement of γ-aminobutyric acid in fermented red seaweed beverage by starter culture Lactobacillus plantarum DW12", Electron J. Biotechnol., 2011, vol. 14, pp. 1-14.
Souza et al., "Neuroprotective effects of sulphated agaran from marine alga *Gracilaria cornea* in rat 6-hydroxydopamine Parkinson's disease model: behavioural, neurochemical and transcriptional alterations", Basic Clin. Pharmacol. Toxicol., 2017, vol. 120, pp. 159-170.

(Continued)

*Primary Examiner* — Michael Barker
(74) *Attorney, Agent, or Firm* — Birch, Stewart, Kolasch & Birch, LLP

(57) ABSTRACT

The present disclosure provides a method for treating and/or alleviating nervous diseases, including: administering an effective amount of a water extract of a plant of Gracilariaceae or a ferment thereof to a subject in need thereof to treat and/or alleviate a nervous disease thereof, wherein the ferment of the water extract of a plant of Gracilariaceae is a lactic acid bacteria ferment.

8 Claims, 10 Drawing Sheets

(56) References Cited

OTHER PUBLICATIONS

Tavares Estevam et al., "Effect of aqueous extract of the seaweed *Gracilaria domingensis* on the physicochemical, microbiological, and textural features of fermented milks", J. Food Sci., 2016, vol. 81, No. 4, pp. C874-C880.

Wu et al., "Growth and survival of lactic acid bacteria during the fermentation and storage of seaweed oligosaccharides solution", J. Mar. Sci. Technol., 2007, vol. 15, No. 2, pp. 104-114.

Extended European Search Report dated Mar. 1, 2019, for European Application No. 18188526.0.

Shao et al., "Antifatigue Effect of Gracilaria Eucheumoides in Mice", Experimental and Therapeutic Medicine, vol. 6, 2013, pp. 1512-1516.

Suzuki et al., "Biological Activities of Gracilaria-Verrucosa", Journal of the Food Hygienic Society of Japan, 1986, XP002788663, 2 pages total.

Chinese Office Action and Search Report, dated Jan. 29, 2021, for Chinese Application No. 201810902320.4.

Hayisama-Ae et al., "A Potential Synbiotic Beverage from Fermented Red Seaweed (*Gracilaria fisheri*) Using Lactobacillus plantarum DW12," International Food Research Journal, vol. 21, No. 5, 2014, pp. 1789-1796.

Japanese Office Action, dated Jul. 14, 2020, for Japanese Application No. 2018-235522.

Tako, "Isolation of Agar from Gracilaria blodgettii HARVEY and Its Gelling Properties," Oyo Toshitsu Kagaku, vol. 41, No. 3, 1994, pp. 305-310, with an English abstract.

Xiao et al., "Study on the Improvement of Milpa Alta Cactus Pectin on Desperate Symptoms in Mice Exposed to Chronic Unpredictable Mild Stress," Modern Journal of Integrated Traditional Chinese and Western Medicine, vol. 24, Aug. 2015 (Aug. 31, 2015), pp. 2630-2631, 2675, with English abstract.

* cited by examiner

Test group A

Test group B

Test group C

Test group D

Test group E

APPLICATION FOR WATER EXTRACT OF PLANT OF *GRACILARIACEAE* OR FERMENT THEREOF AND PHARMACEUTICAL COMPOSITION AND/OR HEALTH FOOD FOR TREATING AND/OR ALLEVIATING NERVOUS DISEASES

TECHNICAL FIELD

The present disclosure is related to applications for a water extract of a plant of Gracilariaceae or a ferment thereof and a pharmaceutical composition and/or health food for treating and/or alleviating nervous diseases.

BACKGROUND

The population over the age of 65 in the world will exceed 2 billion by 2050, and it will account for 20% of the total population. The aging of the population has become an inevitable trend. The increase in the old-age population-dependency ratio will increase the burden of support and cause medical expenditures to increase year by year.

Among the diseases caused by aging, neurodegenerative diseases are taken seriously, and aging accelerates the deterioration of neural-related abilities, such as cognition, rationality, speed, memory, language ability, etc., thereby causing aging-related diseases. According to WHO statistics, more than 20% of the population over the age of 60 suffers from mental or neurological diseases, resulting in 6.6% disability in this ethnic group, wherein the most common elderly neurological or mental illness is Alzheimer's disease, while anxiety affects about 3.8% of this population. These three diseases are all neurodegenerative diseases.

Therefore, blocking or delaying aging and preventing and relieving neurodegenerative diseases are important, urgent issues.

SUMMARY

The present disclosure provides a method for treating and/or alleviating nervous diseases, comprising: administering an effective amount of a water extract of a plant belonging to the family Gracilariaceae or a ferment of the water extract of a plant belonging to the family Gracilariaceae to a subject in need thereof to treat and/or alleviate a nervous disease of the subject, wherein the ferment of the water extract of a plant belonging to the family Gracilariaceae is a ferment formed by a lactic acid bacterium.

The present disclosure also provides a pharmaceutical composition or health food for treating and/or alleviating nervous diseases, comprising: a water extract of a plant belonging to the family Gracilariaceae or a ferment of the water extract of a plant belonging to the family Gracilariaceae, wherein the ferment of the water extract of a plant belonging to the family Gracilariaceae is a ferment formed by a lactic acid bacterium; and a pharmaceutically acceptable carrier or salt.

The present disclosure further provides a method for culturing a microorganism, comprising: culturing a microorganism with a water extract of a plant belonging to the family Gracilariaceae as a culture medium.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein:

FIG. 1A shows the turbidity change of the MRS liquid culture medium or the aqueous solution containing the water extract of *Gracilaria blodgettii* with or without seeding of the activated *Lactobacillus plantarum*. FIG. 1B shows the pH value change of the MRS liquid culture medium or the aqueous solution containing the water extract of *Gracilaria blodgettii* with or without seeding of the activated *Lactobacillus plantarum*. FIG. 1C shows the growth curves of *Lactobacillus plantarum* in the MRS liquid culture medium and the aqueous solution containing the water extract of *Gracilaria blodgettii*. Test group A: MRS liquid culture medium without seeding of bacteria; Test group B: MRS liquid culture medium with seeding of the activated *Lactobacillus plantarum*; Test group C: the aqueous solution containing the water extract of *Gracilaria blodgettii* without seeding of bacteria; Test group D: the aqueous solution containing the water extract of *Gracilaria blodgettii* with seeding of the activated *Lactobacillus plantarum*;

FIG. 4A shows the number of times mice visiting the central area in the open field test. FIG. 4B shows the proportion of time that the mice spent in the central area in the open field test. FIG. 4C shows the total distance the mice moved in the open field test. FIG. 4D shows the number of times the mice reared in the open field test. FIG. 4E shows the moving track of the mice in the open field test. Test group A: the blank group; Test group B: the mice only induced by corticosterone; Test group C: the mice induced by corticosterone and administered with feed containing lactic acid bacteria ($2*10^{10}$ CFU/day); Test group D: the mice induced by corticosterone and administered with feed containing the water extract of *Gracilaria blodgettii* (2 wt %); Test group E: the mice induced by corticosterone and administered with feed containing the ferment of the water extract of *Gracilaria blodgettii* (2 wt %). Statistically significant differences were analyzed by performing analyses of univariate variance of Duncan test using SPSS statistical software (SPSS Institute, Inc., Chicago, Ill., USA). p values less than 0.05 are considered to be a significant difference. There is no significant difference between groups with the same letter elements. There is a significant difference between groups without common element letters.

FIG. 6A shows the time that a mouse spent in the light room. FIG. 6B shows the number of times a mouse entered and exited the light room and the dark room. Test group A: the blank group; Test group B: the mice only induced by corticosterone; Test group C: the mice induced by corticosterone and administered with feed containing lactic acid bacteria ($2*10^{10}$ CFU/day); Test group D: the mice induced by corticosterone and administered with feed containing the water extract of *Gracilaria blodgettii* (2 wt %); Test group E: the mice induced by corticosterone and administered with feed containing the ferment of the water extract of *Gracilaria blodgettii* (2 wt %). Statistically significant differences were analyzed by performing analyses of univariate variance of Duncan test using SPSS statistical software (SPSS Institute, Inc., Chicago, Ill., USA). p values less than 0.05 are considered to be a significant difference. There is no significant difference between groups with the same letter elements. There is a significant difference between groups without common element letters.

FIG. 7A shows the sucrose water preference of the mice in the sucrose water preference test. FIG. 7B shows the total fluid intake of the mice in the sucrose water preference test. Test group A: the blank group; Test group B: the mice only induced by corticosterone; Test group C: the mice induced by corticosterone and administered with feed containing lactic acid bacteria ($2*10^{10}$ CFU/day); Test group D: the mice induced by corticosterone and administered with feed containing the water extract of *Gracilaria blodgettii* (2 wt %); Test group E: the mice induced by corticosterone and administered with feed containing the ferment of the water extract of *Gracilaria blodgettii* (2 wt %). Statistically significant differences were analyzed by performing analyses of univariate variance of Duncan test using SPSS statistical software (SPSS Institute, Inc., Chicago, Ill., USA). p values less than 0.05 are considered to be a significant difference. There is no significant difference between groups with the same letter elements. There is a significant difference between groups without common element letters.

FIG. 8A shows the corticosterone concentration in serum of the mice. FIG. 8B shows the adrenaline concentration in serum of the mice. Test group A: the blank group; Test group B: the mice only induced by corticosterone; Test group C: the mice induced by corticosterone and administered with feed containing lactic acid bacteria ($2*10^{10}$ CFU/day); Test group D: the mice induced by corticosterone and administered with feed containing the water extract of *Gracilaria blodgettii* (2 wt %); Test group E: the mice induced by corticosterone and administered with feed containing the ferment of the water extract of *Gracilaria blodgettii* (2 wt %). Statistically significant differences were analyzed by performing analyses of univariate variance of Duncan test using SPSS statistical software (SPSS Institute, Inc., Chicago, Ill., USA). p values less than 0.05 are considered to be a significant difference. There is no significant difference between groups with the same letter elements. There is a significant difference between groups without common element letters.

DETAILED DESCRIPTION

Figure 1A:
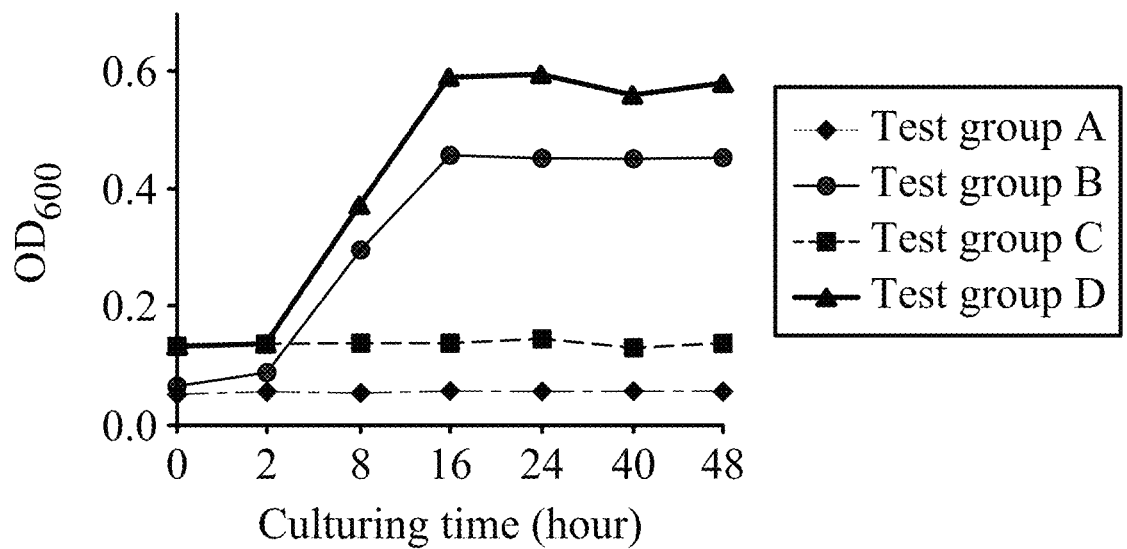
FIGS. 1A-1C show the test results for aqueous solution containing water extract of *Gracilaria blodgettii* with addition of glucose (5% (w/v) the water extract of *Gracilaria blodgettii*+1% (w/v) glucose).

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure provides a method for treating and/or alleviating nervous diseases. The method for treating and/or alleviating nervous diseases may comprise, but is not limited to, administering an effective amount of a water extract of a plant belonging to the family Gracilariaceae or a ferment of the water extract of a plant belonging to the family Gracilariaceae to a subject in need thereof to treat and/or alleviate a nervous disease of the subject.

The nervous disease mentioned above may be any disease related to a nerve without specific limitations, such as depression, bipolar disorder, anxiety, autism, dementia, but it is not limited thereto.

In the method for treating and/or alleviating nervous diseases of the present disclosure, the ferment of the water extract of a plant belonging to the family Gracilariaceae may be a ferment formed by a lactic acid bacterium, but it is not limited thereto.

Examples of the plant belonging to the family Gracilariaceae mentioned above may comprise *Gracilaria blodgettii, Gracilaria coforvoides, Gracilaria gigas, Gracilaria chorda, Gracilaria lichenoides, Gracilaria compressa*, but they are not limited thereto. In one embodiment, the plant belonging to the family Gracilariaceae mentioned above may be *Gracilaria blodgettii*.

Moreover, the foregoing lactic acid bacterium may comprise a bacterium belonging to the genus *Lactobacillus*, but it is not limited thereto. Examples of the foregoing bacterium belonging to the genus *Lactobacillus* may comprise, but are not limited to, *Lactobacillus plantarum, Lactobacillus acidophilus, Lactobacillus bulgaricusk, Lactobacillus gasseri*. In one embodiment, the foregoing lactic acid bacterium may a bacterium belonging to the genus *Lactobacillus* and may be *Lactobacillus plantarum*.

In the method for treating and/or alleviating nervous diseases of the present disclosure, in one embodiment, the foregoing plant belonging to the family Gracilariaceae may be *Gracilaria blodgettii* while the foregoing lactic acid bacterium may be *Lactobacillus plantarum*.

There are no particular limitations on the way to obtain the water extract of a plant belonging to the family Gracilariaceae mentioned above, as long as water is used as the extraction solvent. For example, it can be obtained by any extraction method for water extract of a plant known in the art or it can be obtained by an operator performing the appropriate parameter adjustments depending on the circumstances.

In one embodiment, the water extract of a plant belonging to the family Gracilariaceae mentioned above may be obtained by the step exemplified below, but it is not limited thereto. For example, a procedure of heating under reflux is performed on a plant belonging to the family Gracilariaceae with water to obtain a water extract in the form of extract solution, or a procedure of heating under reflux is performed on a plant belonging to the family Gracilariaceae with water to obtain a water extract solution and the water extract solution is dried to obtain a water extract in the form of extract powder.

In the foregoing embodiment, the weight ratio of the plant belonging to the family Gracilariaceae to the water may be about 1:5-100, such as 1:5-10, 1:10-15, 1:10-20, 1:15-20, but it is not limited thereto. In one specific embodiment, the weight ratio of the plant belonging to the family Gracilariaceae to the water may be about 1:10-15.

Furthermore, in the foregoing embodiment, the temperature of the procedure of heating under reflux may be about 80-100° C., such as 80° C., 85° C., 90° C., 95° C., 100° C., but it is not limited thereto.

In addition, the way to obtain the ferment of the water extract of a plant belonging to the family Gracilariaceae mentioned above has no specific limitations, as long as the water extract of a plant belonging to the family Gracilariaceae is fermented.

In one embodiment, the ferment of the water extract of a plant belonging to the family Gracilariaceae mentioned above may be formed using a method comprising the following steps.

First, an activated lactic acid bacterium is added to an aqueous solution. The aqueous solution mentioned above may contain any foregoing water extract of a plant belonging to the family Gracilariaceae in the form of extract solution, or the aqueous solution mentioned above may formed by adding any foregoing water extract of a plant belonging to the family Gracilariaceae in the form of extract powder to water.

In the foregoing aqueous solution, the content of the foregoing extract powder may be about 1-20% (w/v), such as 1 (w/v), 2% (w/v), 5% (w/v), 8% (w/v), 10% (w/v), but it is not limited thereto.

In one embodiment, the foregoing aqueous solution consists of the foregoing extract solution.

In another embodiment, the foregoing aqueous solution is only formed by adding the foregoing extract powder to water, and in this embodiment, the content of the foregoing extract powder may be about 1-20% (w/v), such as 1% (w/v), 2% (w/v), 5% (w/v), 8% (w/v), 10% (w/v), but it is not limited thereto. In one specific embodiment, in the foregoing aqueous solution, the content of the foregoing extract powder may be about 10% (w/v).

Moreover, in one embodiment, in the step of adding an activated lactic acid bacterium to the aqueous solution mentioned above, in addition to any of the water extracts of a plant belonging to the family Gracilariaceae mentioned above, the foregoing aqueous solution may further comprise a saccharide.

When the foregoing saccharide exists in the foregoing aqueous solution, the foregoing saccharide has no specific limitations, as long as it is a saccharide which can be utilized by a lactic acid bacterium, such as glucose, sucrose, and lactose, but it is not limited thereto. In one embodiment, the foregoing saccharide is glucose. Furthermore, when the foregoing saccharide exists in the foregoing aqueous solution, the content of the foregoing saccharide in the aqueous solution may be about 1-5% (w/v), such as about 1% (w/v), 2% (w/v), 5% (w/v), but it is not limited thereto. In one embodiment, when the foregoing saccharide exists in the foregoing aqueous solution, the content of the foregoing saccharide in the aqueous solution may be about 1% (w/v). In one specific embodiment, when the foregoing saccharide exists in the foregoing aqueous solution, the content of the foregoing extract powder may be about 5% (w/v), and the foregoing saccharide is glucose while the content of the foregoing glucose in the aqueous solution may be about 1% (w/v).

Next, after the step of adding an activated lactic acid bacterium to the aqueous solution mentioned above, a fermentation procedure is performed on the aqueous solution to form the ferment of the water extract of a plant belonging to the family Gracilariaceae.

In the step of performing a fermentation procedure on the aqueous solution to form the ferment of the water extract of a plant belonging to the family Gracilariaceae mentioned above, the temperature of the fermentation procedure mentioned above has no specific limitations, provided is suitable for the growth of the lactic acid bacterium. The temperature of the fermentation procedure mentioned above may be about 34-40° C., such as 34° C., 35° C., 36° C., 36.5° C., 37° C., 37.5° C., 40° C., but it is not limited thereto. In one embodiment, the temperature of the fermentation procedure mentioned above may be about 37° C.

Moreover, in the step of performing a fermentation procedure on the aqueous solution to form the ferment of the water extract of a plant belonging to the family Gracilariaceae mentioned above, the time required for the fermentation procedure mentioned above also has no specific limitation, and can adjusted depending on needs. The time required for the fermentation procedure mentioned may be about 16-72 hours, such as about 16 hours, about 24 hours, about 48 hours, about 72 hours, but it is not limited thereto. In one embodiment, the time required for the fermentation procedure mentioned may be about 48 hours.

In one specific embodiment, in the step of performing a fermentation procedure on the aqueous solution to form the ferment of the water extract of a plant belonging to the family Gracilariaceae mentioned above, the temperature of the fermentation procedure mentioned above may be about 37° C. while the time required for the fermentation procedure mentioned may be about 48 hours.

In addition, in one embodiment, the method for forming the ferment of the water extract of a plant belonging to the family Gracilariaceae mentioned above may further comprise a step of drying the ferment of the water extract of a plant belonging to the family Gracilariaceae after the step of performing a fermentation procedure on the aqueous solution to form the ferment of the water extract of a plant belonging to the family Gracilariaceae.

Moreover, in the method for treating and/or alleviating nervous diseases of the present disclosure, in one embodiment, the plant belonging to the family Gracilariaceae is *Gracilaria blodgettii*, and the ferment of the water extract of a plant belonging to the family Gracilariaceae mentioned above is formed using a method comprising the following steps.

First, activated *Lactobacillus plantarum* is added to an aqueous solution, and the foregoing aqueous solution may contain a water extract of *Gracilaria blodgettii* in the form of extract solution or the foregoing aqueous solution may be formed by adding a water extract of *Gracilaria blodgettii* in the form of extract powder to water.

In one specific embodiment, in the step of adding activated *Lactobacillus plantarum* to an aqueous solution, the foregoing aqueous solution consists of any one of the foregoing extract solutions or the aqueous solution is only formed by adding the extract powder to water. In this specific embodiment, the content of the foregoing extract powder in the aqueous solution may be about 10% (w/v).

In another embodiment, in addition to the water extract of *Gracilaria blodgettii* mentioned above, the foregoing aqueous solution may further comprise glucose. In this specific embodiment, the content of the foregoing extract powder in the aqueous solution may be about 5% (w/v) while the foregoing glucose in the aqueous solution may be about 1% (w/v).

After an activated *Lactobacillus plantarum* is added to an aqueous solution, a fermentation procedure is performed on the aqueous solution to form the ferment of the water extract of a plant belonging to the family Gracilariaceae. The temperature of the fermentation procedure mentioned above may be about 37° C., and the time required for the fermentation procedure mentioned may be about 48 hours.

Furthermore, in one specific embodiment, after an activated *Lactobacillus plantarum* is added to an aqueous solution and a fermentation procedure is performed on the aqueous solution to form the ferment of the water extract of a plant belonging to the family Gracilariaceae, the ferment of the water extract of a plant belonging to the family Gracilariaceae may be further dried.

Any one of the foregoing water extracts of a plant belonging to the family Gracilariaceae or the ferment thereof is capable of reducing stress hormones in serum, and examples of the stress hormones may comprise corticosterone, and adrenaline, but they are not limited thereto.

Moreover, any one of the foregoing water extracts of a plant belonging to the family Gracilariaceae or the ferment thereof has the effect of alleviating emotional reactions.

In any of the above-mentioned methods for treating and/or alleviating nervous diseases of the present disclosure, the subject may include, but is not limited to, a vertebrate. Moreover, the vertebrate mentioned above may include a fish, an amphibian, a reptile, a bird, or a mammal, but it is not limited thereto. Examples of the mammal may include, but are not limited to, a human, an orangutan, a monkey, a horse, a donkey, a dog, a cat, a rabbit, a guinea pig, a rat, and a mouse. In one embodiment, in any above-mentioned method for treating and/or alleviating nervous diseases of the present disclosure, the subject is a human.

In addition, the present disclosure also provides a pharmaceutical composition and/or health food for treating and/or alleviating nervous diseases. The nervous disease mentioned herein may be any disease related to a nerve without specific limitations, such as depression, bipolar disorder, anxiety, autism, dementia, but it is not limited thereto.

The pharmaceutical composition or health food for treating and/or alleviating nervous diseases of the present disclosure mentioned above, may comprise, but is not limited to, a water extract of a plant belonging to the family Gracilariaceae or a ferment of the water extract of a plant belonging to the family Gracilariaceae and a pharmaceutically acceptable carrier or salt.

The water extract of a plant belonging to the family Gracilariaceae or a ferment thereof contained by the pharmaceutical composition and/or health food for treating and/or alleviating nervous diseases of the present disclosure can be any one of the foregoing water extracts of a plant belonging to the family Gracilariaceae or the ferment thereof described in the above paragraphs related to the method for treating and/or alleviating nervous diseases of the present disclosure, and thus it is not repeated here.

The pharmaceutically acceptable carrier mentioned above may comprise, but is not limited to, a solvent, a dispersion medium, a coating, an antibacterial and antifungal agent, or an isotonic and absorption delaying agent, etc. which is suitable for pharmaceutical administration. The pharmaceutical composition can be formulated into dosage forms for different administration routes utilizing conventional methods.

Furthermore, the pharmaceutically acceptable salt mentioned above may include, but is not limited to, salts including inorganic cation, such as alkali metal salts such as sodium salt, potassium salt or amine salt, such as alkaline-earth metal salt such as magnesium salt or calcium salt, such as the salt containing bivalent or quadrivalent cation such as zinc salt, aluminum salt or zirconium salt. In addition, the pharmaceutically acceptable salt may also be organic salt, such as dicyclohexylamine salt, methyl-D-glucamine, and amino acid salt such as arginine, lysine, histidine, or glutamine.

The pharmaceutical composition of the present disclosure may be administered orally, parenterally by an inhalation spray, or via an implanted reservoir. The parenteral methods may comprise smearing affected regions, subcutaneous, intracutaneous, intravenous, intramuscular, intra-articular, intra-arterial, intrasynovial, intrasternal, intrathecal, and intraleaional injection, as well as infusion techniques.

An oral composition may include, but is not limited to, tablets, capsules, emulsions, and aqueous suspensions, dispersions and solutions.

Furthermore, the present disclosure further provides a method for culturing a microorganism. The method for culturing a microorganism mentioned above may comprise, but is not limited to, culturing a microorganism with a water extract of a plant belonging to the family Gracilariaceae as a culture medium.

The microorganism mentioned above has no specific limitations, as long as it can utilize a water extract of a plant belonging to the family Gracilariaceae for growth, such as a bacterium. In one embodiment, the bacterium may be a bacterium belonging to the genus *Lactobacillus*, such as *Lactobacillus plantarum, Lactobacillus acidophilus, Lactobacillus bulgaricusk, Lactobacillus gasseri*, but it is not limited thereto. In one specific embodiment, the microorganism mentioned herein is *Lactobacillus plantarum*.

Moreover, the water extract of a plant belonging to the family Gracilariaceae described in the method for culturing a microorganism of the present disclosure also can be any one of the foregoing water extracts of a plant belonging to the family Gracilariaceae described in the above paragraphs related to the method for treating and/or alleviating nervous diseases of the present disclosure, and thus it is not repeated here.

In the method for culturing a microorganism of the present disclosure, the culture medium may contain any of the foregoing water extract of a plant belonging to the family Gracilariaceae in the form of extract solution, or the culture medium may be formed by adding any of the foregoing water extract of a plant belonging to the family Gracilariaceae in the form of extract powder to water. The content of the foregoing extract powder in the culture medium may be about 1-20% (w/v), such as 1% (w/v), 2% (w/v), 5% (w/v), 8% (w/v), 10% (w/v), but it is not limited thereto.

In one embodiment, the foregoing culture medium consists of the foregoing extract solution.

In another embodiment, the foregoing culture medium is only formed by adding the foregoing extract powder to water, and in this embodiment, the content of the foregoing extract powder may be about 1-20% (w/v), such as 1% (w/v), 2% (w/v), 5% (w/v), 8% (w/v), 10% (w/v), but it is not limited thereto. In one specific embodiment, in the foregoing aqueous solution, the content of the foregoing extract powder may be about 10% (w/v).

Moreover, in one embodiment, in the method for culturing a microorganism of the present disclosure, in addition to any one of the water extracts of a plant belonging to the family Gracilariaceae mentioned above, the foregoing culture medium may further comprise a saccharide.

When the foregoing saccharide exists in the foregoing culture medium, the foregoing saccharide has no specific limitations, as long as it is a saccharide which can be utilized by a microorganism, such as glucose, sucrose, lactose, but it is not limited thereto. In one embodiment, the foregoing saccharide is glucose. Furthermore, when the saccharide exists in the foregoing culture medium, the content of the foregoing saccharide in the culture medium may be about 1-5% (w/v), such as about 1% (w/v), 2% (w/v), 5% (w/v), but it is not limited thereto. In one embodiment, when the saccharide exists in the foregoing culture medium, the content of the foregoing saccharide in the culture medium may be about 1% (w/v). In one specific embodiment, when the saccharide exists in the foregoing culture medium, the foregoing saccharide is glucose while the content of the foregoing glucose in the culture medium may be about 1% (w/v).

In the method for culturing a microorganism of the present disclosure, in one embodiment, the culture medium is used for culturing *Lactobacillus plantarum*.

In the embodiment in which the culture medium is used for culturing *Lactobacillus plantarum*, the foregoing culture medium may consist of any one of the extract solutions mentioned above, or the foregoing culture medium is only formed by adding any one of the water extracts of a plant belonging to the family Gracilariaceae mentioned above in the form of extract powder to water. The content of the foregoing extract powder may be about 10% (w/v).

Alternatively, in the embodiment in which the culture medium is used for culturing *Lactobacillus plantarum*, in addition to any one of the water extracts of a plant belonging to the family Gracilariaceae mentioned above, the foregoing culture medium may further comprise glucose. The content of the foregoing extract powder in the culture medium may be about 5% (w/v) while the content of the foregoing glucose may be about 1% (w/v).

In the method for culturing a microorganism of the present disclosure, the temperature suitable for culturing a microorganism by the culture medium has no specific limitations and it can depend on the microorganism to be cultured. In one embodiment, the temperature suitable for culturing a microorganism may be about 34-40° C., such as 34° C., 35° C., 36° C., 36.5° C., 37° C., 37.5° C., 40° C., but it is not limited thereto. In one specific embodiment, the foregoing temperature suitable for culturing a microorganism may be about 37° C.

Furthermore, in the method for culturing a microorganism of the present disclosure, the time suitable for culturing a microorganism by the culture medium also has no specific limitations and it can depend on the microorganism to be cultured, similarly. In one embodiment, the time suitable for culturing a microorganism by the culture medium may be about 16-72 hours, such as about 16 hours, about 24 hours, about 48 hours, about 72 hours, but it is not limited thereto. In one specific embodiment, the time suitable for culturing a microorganism by the culture medium may be about 48 hours.

EXAMPLES

Example 1

Preparation of Water Extract of *Gracilaria blodgettii*

*Gracilaria blodgettii* was placed in 10-15 times its weight of deionized water and heated under reflux at 80-100° C. for 1-2 hours for performing extraction to obtain an extract solution. After the extract solution was suction-filtered with filter paper, the extract solution was concentrated with a vacuum concentrator and lyophilized with a vacuum dryer to remove moisture to obtain an extract powder.

Example 2

Use of Water Extract of *Gracilaria blodgettii* as Culture Medium (Fermentation of Water Extract of *Gracilaria blodgettii*)

Example 2-1

Test for Aqueous Solution Containing Water Extract of *Gracilaria blodgettii* with Addition of Glucose A. Methods 1. A bacterial cell suspension of *Lactobacillus plantarum* (product name: *Lactobacillus plantarum* (LP28), purchased from SYNBIO TECH INC., Taiwan) (the bacterial cell suspension: $1\times10^5$ CFU/mL) was seeded to a sterilized MRS liquid culture medium (Sigma, Cat No. 69966) at a 1% (v/v) (volume ratio of the bacterial cell suspension to the liquid culture medium was 1:99) of bacterial seeding amount, and placed in a 37° C. incubator for culturing for 12-18 hours to activate the bacteria.

2. The bacterial cell suspension of the activated *Lactobacillus plantarum* (the bacterial cell suspension: $1\times10^5$ CFU/mL) was seeded at a 1% (v/v) of bacterial seeding amount or was not seeded to a sterilized MRS liquid culture medium or an aqueous solution containing the water extract of *Gracilaria blodgettii* (the aqueous solution contained 5% (w/v) the water extract of *Gracilaria blodgettii* in the form of extract powder obtained above and 1% (w/v) glucose) to generate 4 test groups which were Test group A, Test group B, Test group C and Test group D. Test group A was MRS liquid culture medium without seeding of bacteria (the blank group for MRS liquid culture), Test group B was MRS liquid culture medium with seeding of the activated *Lactobacillus plantarum* (the experimental group for MRS liquid culture), Test group C was the aqueous solution containing the water extract of *Gracilaria blodgettii* without seeding of bacteria (the blank group for the aqueous solution containing the water extract of *Gracilaria blodgettii*), and Test group D was the aqueous solution containing the water extract of *Gracilaria blodgettii* with seeding of the activated *Lactobacillus plantarum* (the experimental group for the aqueous solution containing the water extract of *Gracilaria blodgettii*).

3. The four test groups were placed in a 37° C. incubator for culturing for 48 hours. Sampling was performed during the culturing at default time points. Absorbance on wavelength 600 nm ($OD_{600}$) and pH value of the sample of each time point were determined. Moreover, after being appropriately diluted, the sample of each time point was plated on a MRS solid culture medium. Next, the MRS solid culture medium plated with bacterial suspension was placed in a 37° C. incubator for culturing for 48 hours, and then the number of bacteria in the sample at each time point was calculated.

B. Results

Figure 1B:
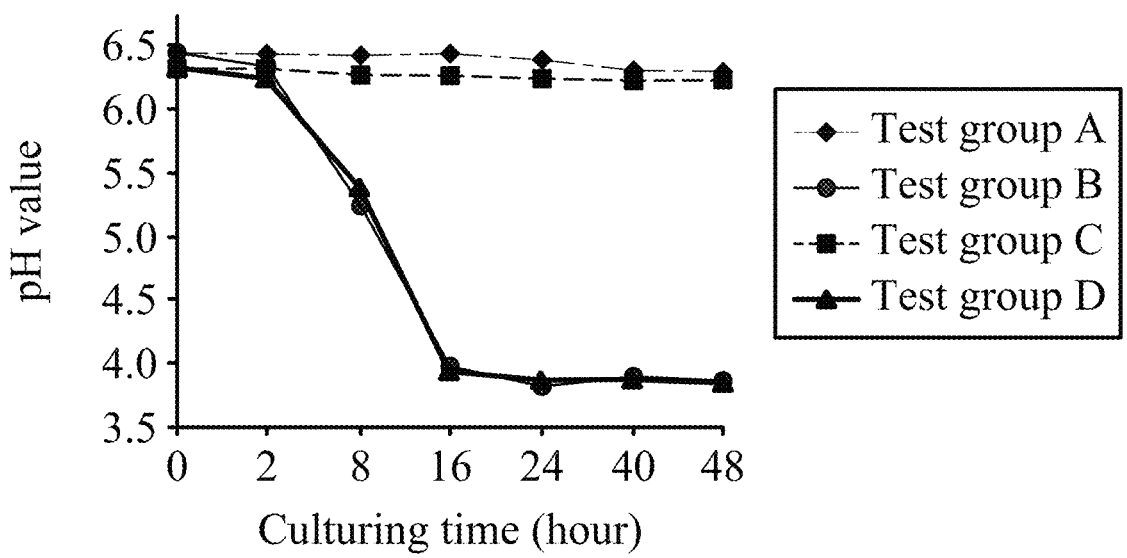
Figure 1C:
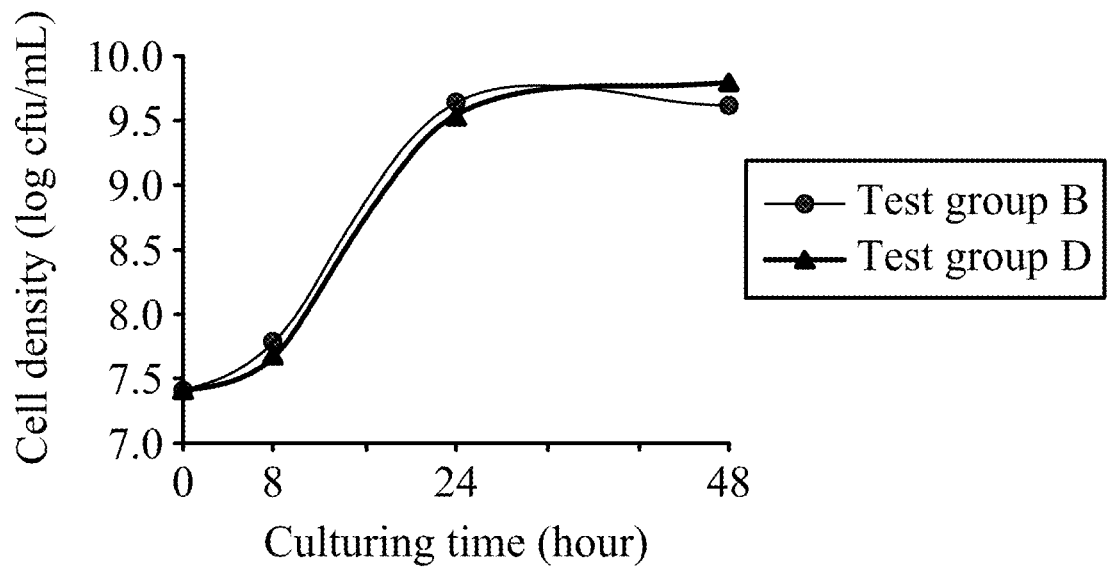

Absorbance change and pH value change for each test group are shown in FIG. 1A and FIG. 1B, respectively. Bacterial amount change for each test group is shown in FIG. 1C.

According to FIG. 1A, it is known that the turbidity of the aqueous solution containing the water extract of *Gracilaria blodgettii* with seeding of the activated *Lactobacillus plantarum* (Test group D) increases with the extension of culturing time, and the trend of turbidity change for the aqueous solution containing the water extract of *Gracilaria blodgettii* with seeding of the activated *Lactobacillus plantarum* (Test group D) is similar to that of MRS liquid culture medium with seeding of the activated *Lactobacillus*

*plantarum* (Test group B), and this shows that *Lactobacillus plantarum* has a similar growth trend in the aqueous solution containing the water extract of *Gracilaria blodgettii* and in MRS liquid culture medium. Moreover, based on FIG. 1A, it is known that the turbidity of the Test group A and the Test group C do not increase, and this represents that the MRS liquid culture medium and the aqueous solution of the water extract of *Gracilaria blodgettii* are not contaminated by other bacteria.

According to FIG. 1B, it is known that the pH value of the aqueous solution containing the water extract of *Gracilaria blodgettii* with seeding of the activated *Lactobacillus plantarum* (Test group D) decreases with the extension of culturing time and the trend of pH change for the aqueous solution containing the water extract of *Gracilaria blodgettii* with seeding of the activated *Lactobacillus plantarum* (Test group D) is similar to that of MRS liquid culture medium with seeding of the activated *Lactobacillus plantarum* (Test group B), and this represents the increase of lactic acid which is the main product of the lactic acid bacteria. Moreover, based on FIG. 1B, it is known that there is almost no change in the solutions of the Test group A and the Test group C, and this represents that the MRS liquid culture medium and the aqueous solution of the water extract of *Gracilaria blodgettii* are not contaminated by other bacteria.

According to FIG. 1C, it is known that the bacterial amount and growth rate of the *Lactobacillus plantarum* cultured by the aqueous solution containing the water extract of *Gracilaria blodgettii* (Test group D) are similar to those of the *Lactobacillus plantarum* cultured by MRS liquid culture medium (Test group B), and this shows that the water extract of *Gracilaria blodgettii* can provide a sufficient of nutrient source for the growth of *Lactobacillus plantarum* and can be used as a culture medium instead of a standard culture medium.

Example 2-1

Test for Aqueous Solution Containing Water Extract of *Gracilaria blodgettii* without Addition of Glucose
A. Methods
1. A bacterial cell suspension of *Lactobacillus plantarum* (product name: *Lactobacillus plantarum* (LP28), purchased from SYNBIO TECH INC., Taiwan) (the bacterial cell suspension: $1 \times 10^5$ CFU/mL) was seeded to a sterilized MRS liquid culture medium (Sigma, Cat No. 69966) at a 1% (v/v) (volume ratio of the bacterial cell suspension to the liquid culture medium was 1:99) of bacterial seeding amount, and placed in a 37° C. incubator for culturing for 12-18 hours to activate the bacteria.
2. The bacterial cell suspension of the activated *Lactobacillus plantarum* (the bacterial cell suspension: $1 \times 10^5$ CFU/mL) was seeded at a 1% (v/v) of bacterial seeding amount to a sterilized MRS liquid culture medium or an aqueous solution containing the water extract of *Gracilaria blodgettii* (the aqueous solution contained 10% (w/v) the water extract of *Gracilaria blodgettii* in the form of extract powder obtained above) to generate 2 test groups which were Test group A and Test group B. Test group A was MRS liquid culture medium with seeding of the activated *Lactobacillus plantarum* and Test group B was the aqueous solution containing the water extract of *Gracilaria blodgettii* with seeding of the activated *Lactobacillus plantarum*.
3. The two test groups were placed in a 37° C. incubator for culturing for 48 hours. Sampling was performed during the culturing at default time points. After being appropriately diluted, the sample of each time point was plated on a MRS solid culture medium. Next, the MRS solid culture medium plated with bacterial suspension was placed in a 37° C. incubator for culturing for 48 hours, and then the number of bacteria in the sample at each time point was calculated.
B. Results
Bacterial amount change for each test group is shown in FIG. 2.

Figure 2:
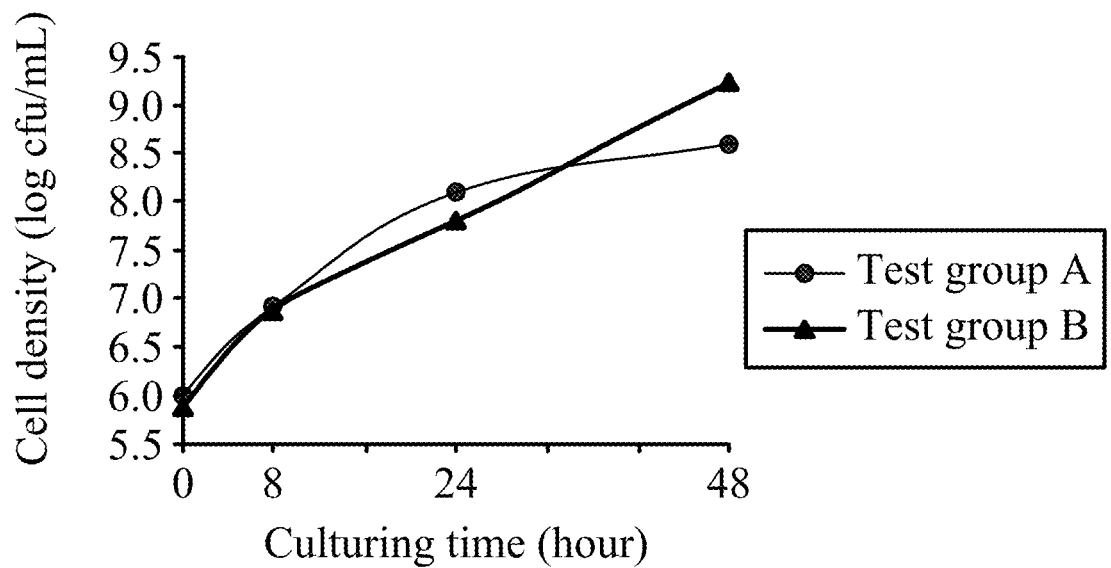
FIG. 2 shows the growth curves of *Lactobacillus plantarum* in the MRS liquid culture medium and the aqueous solution containing the water extract of *Gracilaria blodgettii* (10% (w/v) the water extract of *Gracilaria blodgettii*). Test group A: MRS liquid culture medium with seeding of the activated *Lactobacillus plantarum*; Test group B: the aqueous solution containing the water extract of *Gracilaria blodgettii* with seeding of the activated *Lactobacillus plantarum*.

According to FIG. 2, it is known that *Lactobacillus plantarum* can grow well in both of the aqueous solution containing the water extract of *Gracilaria blodgettii* (Test group B) and MRS liquid culture medium (Test group A), and this shows that the water extract of *Gracilaria blodgettii* can provide a sufficient of nutrient source for the growth of *Lactobacillus plantarum* and can be used as a culture medium instead of a standard culture medium.

Based on the results of Example 2-1 and Example 2-2, it is clearly known that whether or not there is an addition of glucose, the water extract of *Gracilaria blodgettii* can be used as a culture medium and make *Lactobacillus plantarum* grow well.

Example 3

Evaluations of Water Extract of *Gracilaria blodgettii* and Ferment Thereof on Improvement of Mouse Behavior in Open Field Test
A. Methods
7-8 week-old BALB/c male mice were divided into 5 groups which were Test group A, Test group B, Test group C, Test group D and Test group E. Test group A was a blank group.

The mice of Test group B, Test group C, Test group D and Test group E were subcutaneously injected with corticosterone (CORT) (40 mg/kg/day) for 28 continuous days to induce depression-like/anxiety-like symptoms of the mice, and the mice of the blank group was subcutaneously injected with soybean oil for 28 continuous days.

On Day 15, providing of common feed (Test group A and Test group B), feed containing lactic acid bacteria ($2*10^{10}$ CFU/day) (Test group C), feed containing the water extract of *Gracilaria blodgettii* (2 wt %) (Test group D) or feed containing the ferment of the water extract of *Gracilaria blodgettii* (2 wt %) (Test group E) to the mice was started. In the Test group B, the mice are only induced by corticosterone.

The subcutaneous injection of corticosterone to the mice is still maintained during feed administration.

14 days after starting to feed the feed sample, open field test was performed on the mice to evaluate the behavior of the mice.

Open field test is the most commonly used animal behavior analysis method, currently. According to ethology, rodents have a thimmotaxis for a new environment. The central area is open and that means a threat situation while the peripheral area is relatively safe, and thus rodents naturally have a tendency to close the peripheral area to move.

Figure 3A:
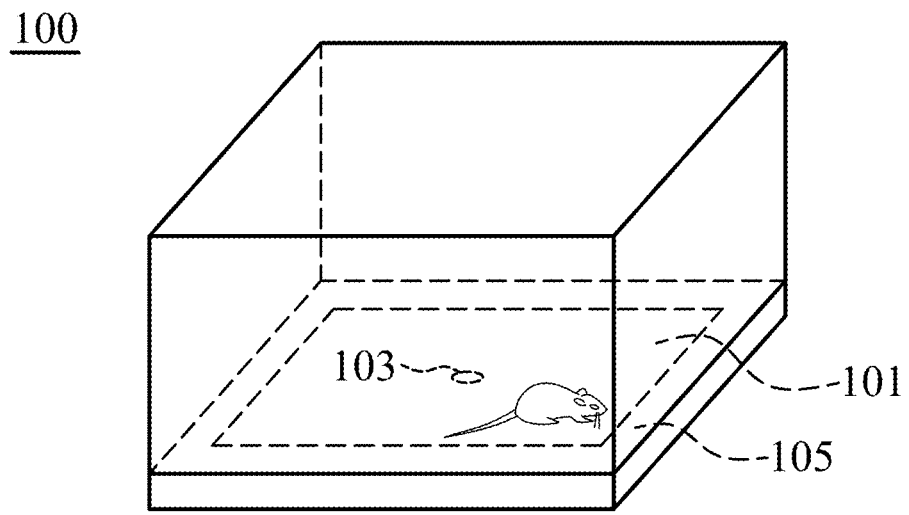
FIG. 3A is a schematic diagram of the overall appearance of a test box 100 used for the open field test of one embodiment of the present disclosure.
Figure 3B:
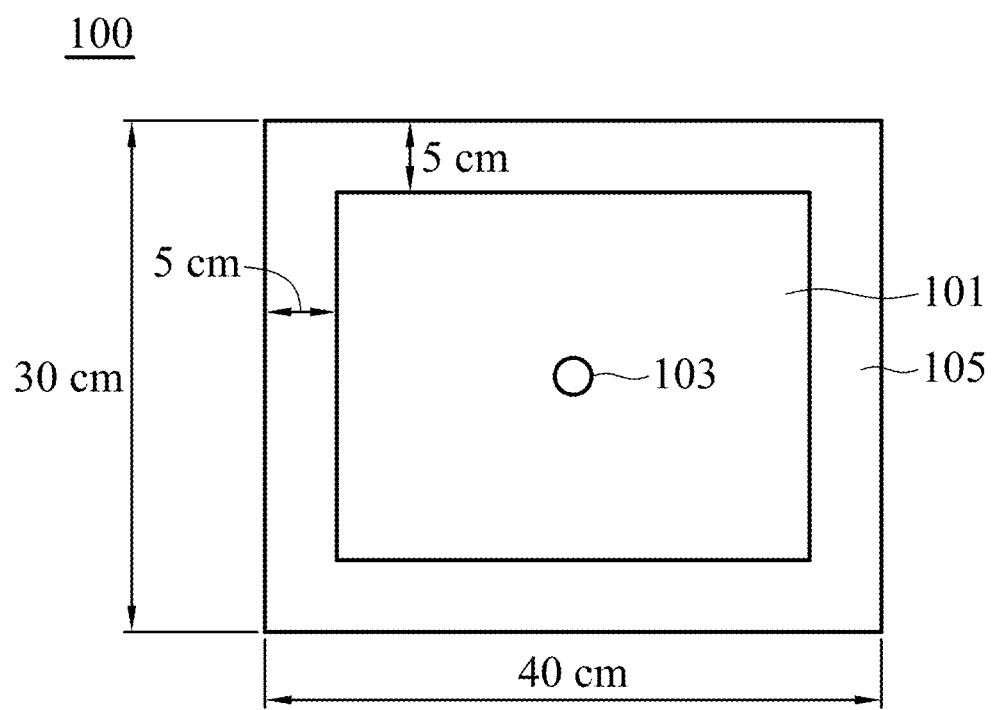
FIG. 3B is a schematic diagram of the bottom of the interior of a test box 100 used for the open field test of one embodiment of the present disclosure.

Open field test was performed in a test box 100 shown in FIG. 3A. FIG. 3B shows the bottom of the interior of the test box 100. The length of the test box was 40 cm, the width was 30 cm and height was 15 cm. Referring to FIG. 3B, the interior of the test box was divided into a central area 101 and a peripheral area 103. The central area 101 located on a rectangular region of the central part of the bottom of the test box and it had a center point 103. The peripheral area 105 located on the periphery of the central area 101 and surrounded the central area 101, and had a width of 5 cm.

Photography was performed during the test, and the record and analysis were performed by the animal behavior tracking analysis system (Noldus Ethovision XT, 10th edition).

The mouse was placed on the central point (starting point) of the central area of the test box 100 and the observation was started. The number of times the mice crossed each area, the proportion of time spent in the central area, the total distance moved, and the number of times the mice reared within a 5-minute period were recorded. In general, rodents tend to move on the periphery, and if the number of times and time spent in the central area increases, that means that the degree of depression/anxiety is reduced. Emotional responses of the experimental animals were evaluated by the activity of the experimental animals in the central area and the peripheral area.

B. Results

Figure 4A:
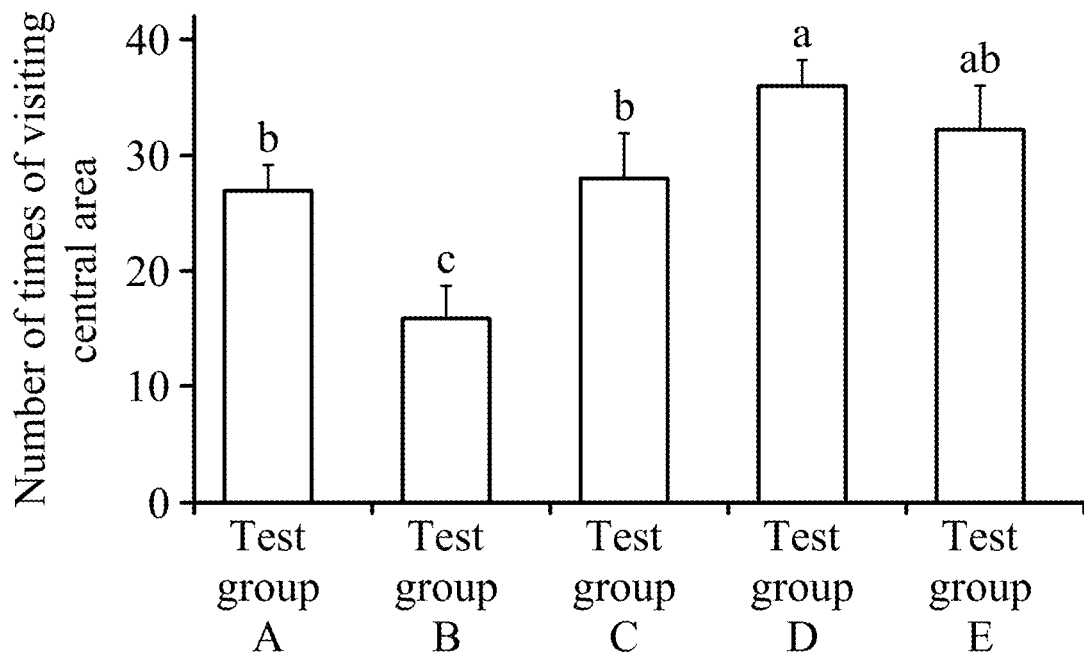
FIGS. 4A-4E show the results of the open field test of one embodiment of the present disclosure.
Figure 4B:
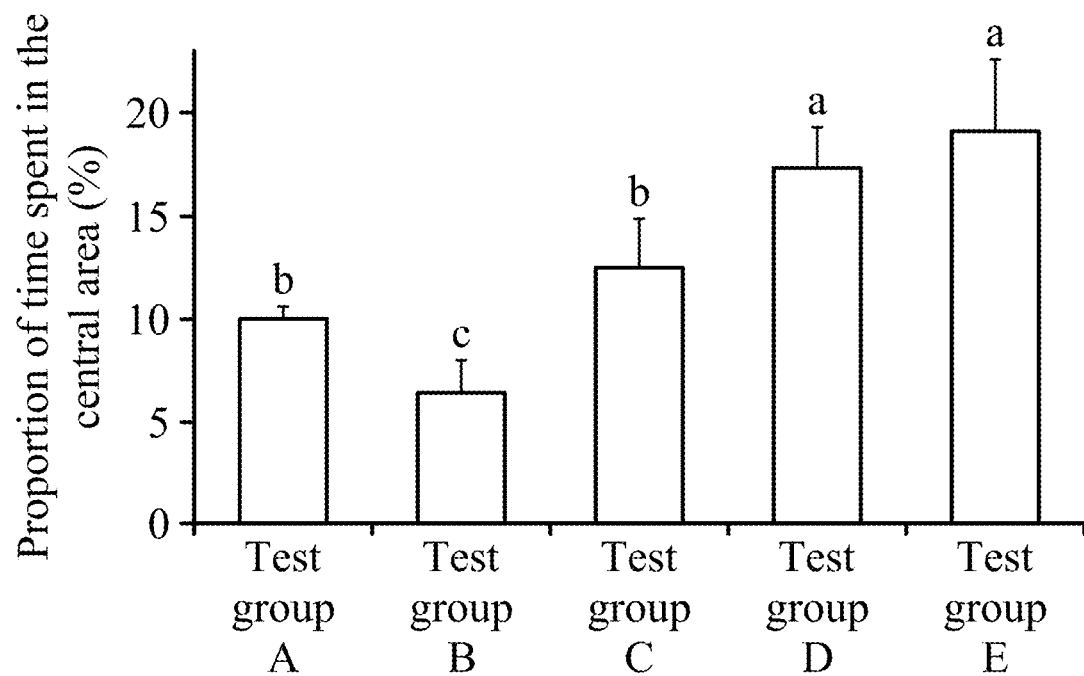
Figure 4C:
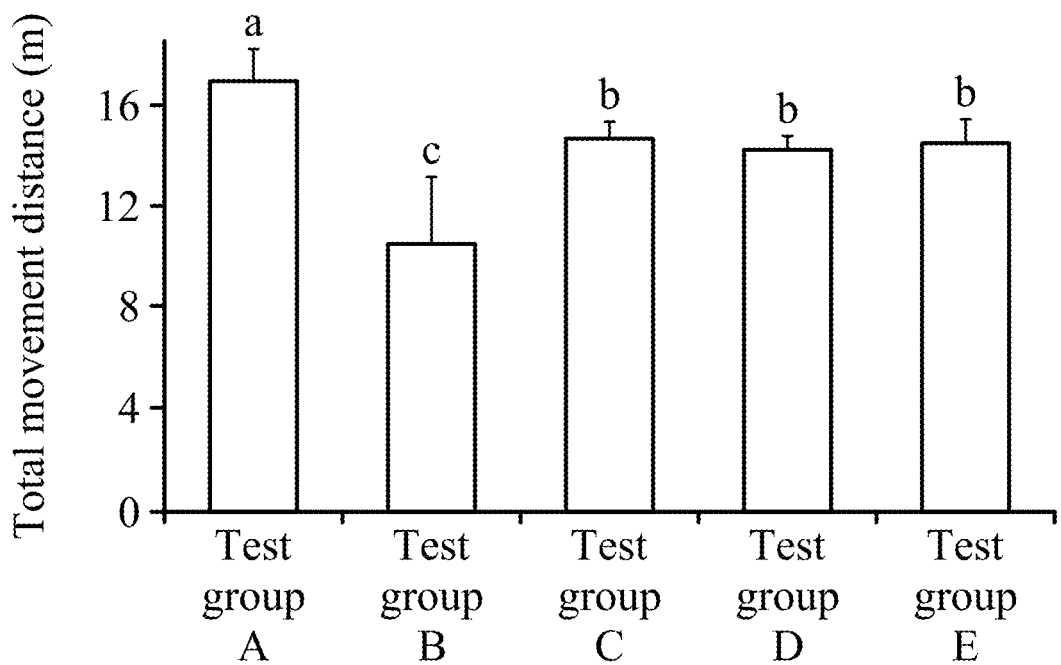
Figure 4D:
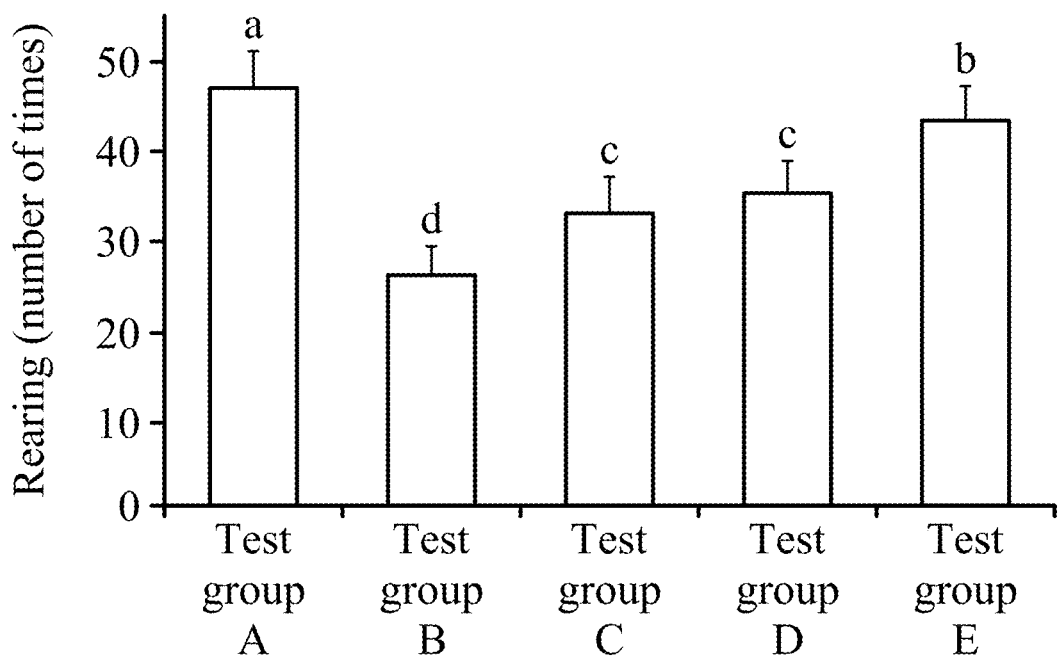
Figure 4E:
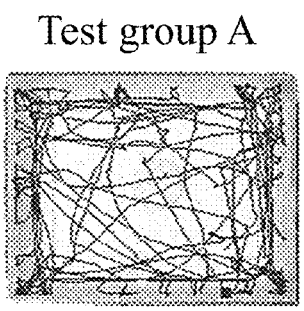
Figure 4E:
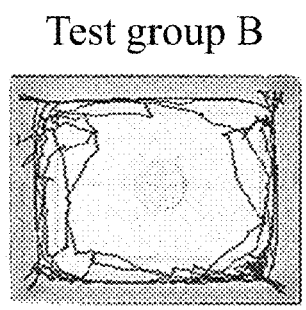
Figure 4E:
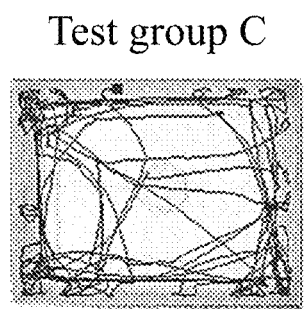
Figure 4E:
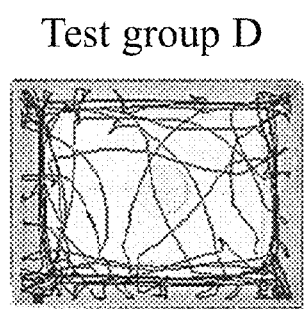
Figure 4E:
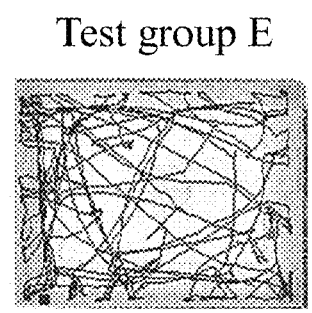

The results of the open field test are shown in FIGS. 4A-4E. FIG. 4A shows the number of times of the mice visiting the central area, FIG. 4B shows the proportion of time that the mice spent in the central area, FIG. 4C shows the total distance moved by the mice, FIG. 4D shows the number of times the mice reared, and FIG. 4E shows the moving track of the mice.

According to the experimental results shown in FIGS. 4A-4E, it is known that, compared to the mice of the blank group (Test group A), the number of times of visits to the central area (FIG. 4A) and the proportion of time spent in the central area (FIG. 4B) for the mice only induced by corticosterone (Test group B) are significantly reduced ($p<0.05$). Moreover, compared to the mice of the blank group (Test group A), the total distance moved by the mice (FIG. 4C) and the number of times the mice reared (FIG. 4D) when only induced by corticosterone (Test group B) are also significantly reduced ($p<0.05$).

The above results show that the mice with depression-like/anxiety-like symptoms will quickly move to the periphery to find shelter to seek protection. As a result, time spent in the central area and the total distance that the mice move will be significantly reduced, and the decrease in the number of times the mice rear represents a decline in exploration behavior.

Furthermore, according to the experimental results shown in FIGS. 4A-4E, it is known that, compared to the mice only induced by corticosterone (Test group B), the number of times of visits to the central area (FIG. 4A) and the proportion of time spent in the central area (FIG. 4B) for the mice orally administered with lactic acid bacteria (Test group C), the water extract of *Gracilaria blodgettii* (Test group D) or the ferment of the water extract of *Gracilaria blodgettii* formed by the lactic acid bacteria (Test group E) are significantly recovered ($p<0.05$). In addition, compared to the mice only induced by corticosterone (Test group B), the mice orally administered with lactic acid bacteria (Test group C), the water extract of *Gracilaria blodgettii* (Test group D) or the ferment of the water extract of *Gracilaria blodgettii* formed by the lactic acid bacteria (Test group E) also show significantly higher walking intention (FIG. 4C) ($p<0.05$) and the rearing times thereof also significantly increased (FIG. 4D) ($p<0.05$).

The above results show that oral administration of lactic acid bacteria, the water extract of *Gracilaria blodgettii* or the ferment of the water extract of *Gracilaria blodgettii* formed by the lactic acid bacteria can promote the mice's curiosity and exploration of the outside world. The effect of recovering the proportion of time that the mice spent in the central area of the ferment of the water extract of *Gracilaria blodgettii* formed by the lactic acid bacteria seems to be better than that of lactic acid bacteria or the water extract of *Gracilaria blodgettii* (FIG. 4B), and the effect of raising the number of times of mouse rearing of the ferment of the water extract of *Gracilaria blodgettii* formed by the lactic acid bacteria is significantly better than that of the lactic acid bacteria and the water extract of *Gracilaria blodgettii* (FIG. 4D) ($p<0.05$).

Example 4

Evaluations of Water Extract of *Gracilaria blodgettii* and Ferment Thereof on Improvement of Mouse Behavior in Light-Dark Box (LDB) Test A. Methods The mice of each group of Example 3 were used to perform this experiment.

14 days after starting to feed the feed sample, light-dark box test was performed on the mice to evaluate the behavior of the mice.

Rodents have the biological characteristics of instinctive behavior of disliking and avoidance of bright light, and thus the change of behavior in mice can be evaluated by the light-dark box test.

Figure 5:
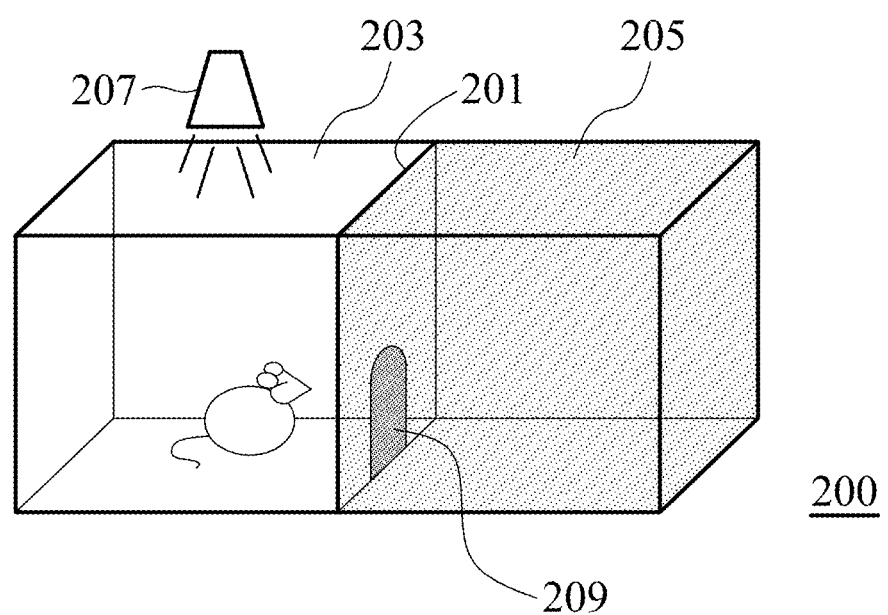
FIG. 5 is a schematic diagram of a test box 200 used for the light-dark (LDB) box test of one embodiment of the present disclosure.

The light-dark box test was performed in a test box 200 shown in FIG. 5. The interior of the test box 200 was divided into a light room 203 and a dark room 205 by a separator 201. In the light room, a light source 207 was configured to keep the light room 203 light while in the dark room, the dark was kept. A door 209 was configured at the bottom of the separator 201 to allow the mouse to be able to freely move between the light room and the dark room. Photography was performed during the test, and the record and analysis were performed by the animal behavior tracking analysis system (Noldus Ethovision XT, 10th edition).

The mouse is placed in the light room 203 in the test box 200 with the head facing a direction back on the door 209 and the observation was started. Time that the mouse spent in the light room and the number of times the mouse entered and exited the light room and the dark room within a 5-minute period were recorded. Generally, rodents tend to move in a darkroom, and if the number of times and the duration of a rodent staying in the light room increase and/or the number of conversions in the light and dark room increases, that means that the degree of depression/anxiety is reduced. Emotional responses of the experimental animals were evaluated by the activity of the experimental animals in the light room and the dark room.

B. Results

Figure 6A:
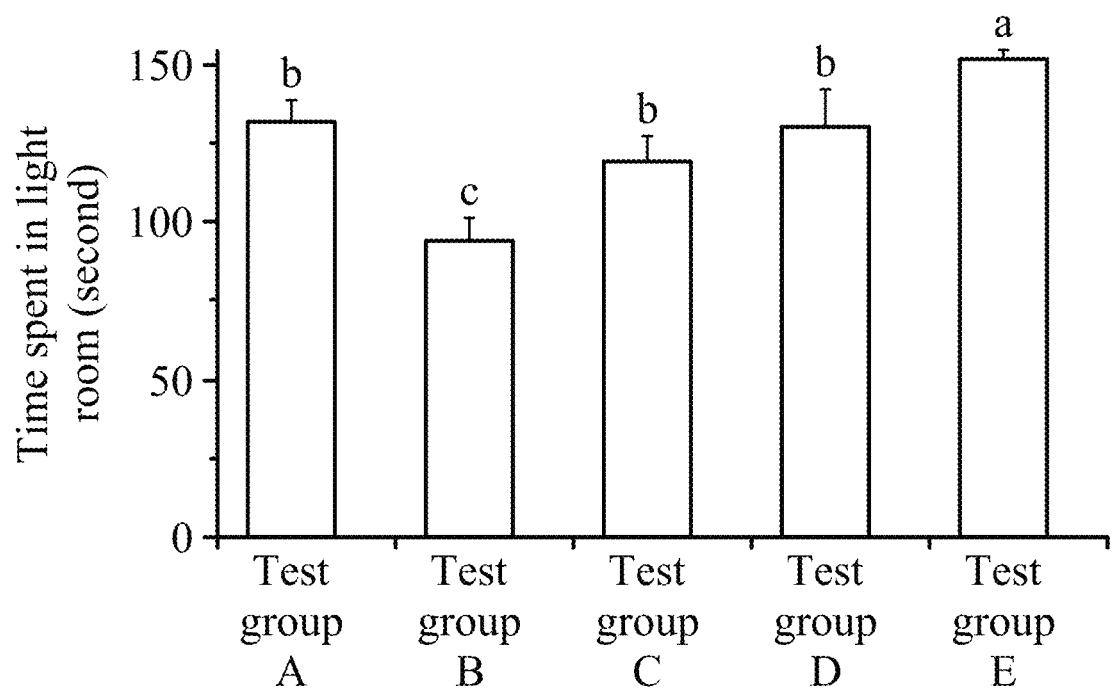
FIGS. 6A and 6B show the results of the light-dark box test of one embodiment of the present disclosure.
Figure 6B:
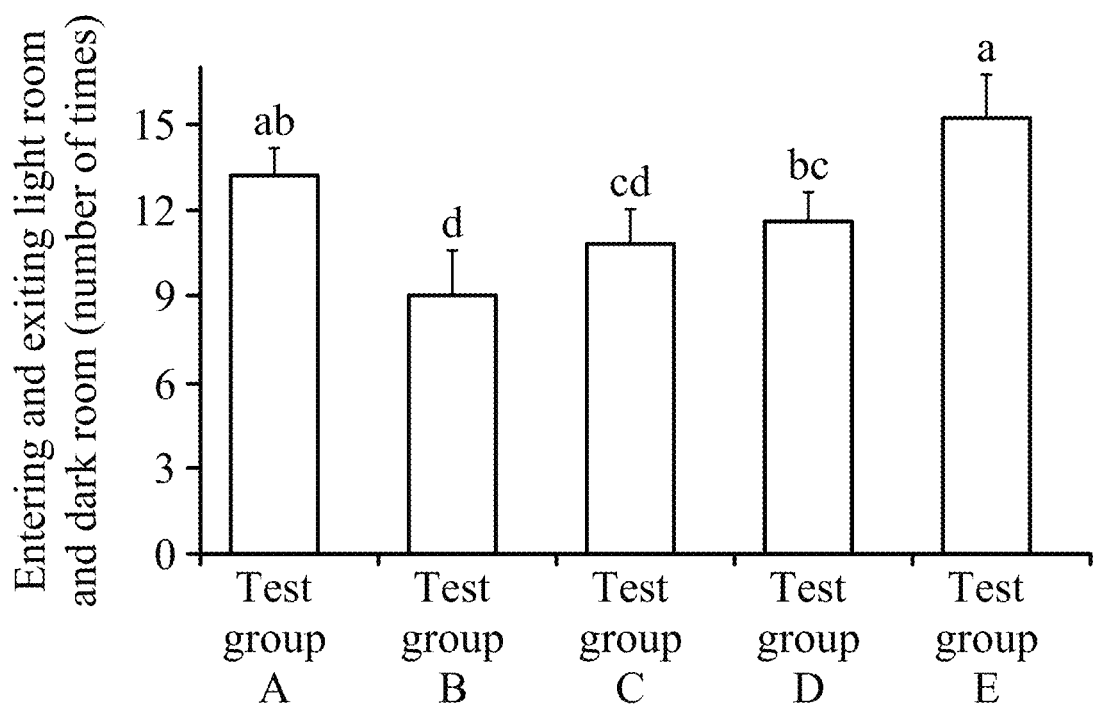

The results of the light-dark box test are shown in FIGS. 6A and 6B. FIG. 6A shows the time that a mouse spent in the light room, and FIG. 6B shows the number of times the mouse entered and exited the light room and the dark room.

According to the experimental results shown in FIGS. 6A and 6B, it is known that the time spent in the light room (FIG. 6A) and the number of times entering and exiting the light room and the dark room (FIG. 6B) of the mice only induced by corticosterone (Test group B) are significantly less than those of the mice of the blank (Test group A) ($p<0.05$).

The above results show that the mice with depression-like/anxiety-like symptoms have reduced inclination to stay in the light room.

According to the experimental results shown in FIGS. 6A and 6B, it is known that, compared to the mice only induced by corticosterone (Test group B), the time spent in the light room and the number of times entering and exiting the light room and the dark room for the mice orally administered with lactic acid bacteria (Test group C), the water extract of *Gracilaria blodgettii* (Test group D) or the ferment of the water extract of *Gracilaria blodgettii* formed by the lactic acid bacteria (Test group E) are significantly increased (p<0.05).

The above results show that oral administration of lactic acid bacteria, the water extract of *Gracilaria blodgettii* or the ferment of the water extract of *Gracilaria blodgettii* formed by the lactic acid bacteria can raise the inclination of the mouse to move to the light room and/or stay in the light room. In addition, the effects of increasing the time that the mouse spent in the light room and the number of times the mouse entered and exited the light room and the dark room of the ferment of the water extract of *Gracilaria blodgettii* formed by the lactic acid bacteria is significantly better than those of the lactic acid bacteria and the water extract of *Gracilaria blodgettii* (p<0.05).

Example 5

Evaluations of Water Extract of *Gracilaria blodgettii* and Ferment Thereof on Improvement of Mouse Behavior in Sucrose Water Preference Test A. Methods The mice of each group of Example 3 were used to perform this experiment.

14 days after starting to feed the feed sample, sucrose water preference test was performed on the mice to evaluate the behavior of the mice.

Rodents generally have hedonic behavior, and they tend to drink sugary water more than sugar-free water. If the rodent's sugar water preference increases, it means that the degree of depression/anxiety is reduced.

Sucrose water with a sucrose content of 1% (w/v) and common sugar-free water were simultaneously provided during the test, the mice were free to ingest two liquids, and the test time is 24 hours. After the end of the test, the respective intakes of sucrose water and common sugar-free water of the mice were calculated and summed to obtain the total fluid intake of the mice, and the mice's selectivity to sucrose water within 24 hours was evaluated. Sucrose water preference (%) was calculated by the formula shown below:

Sucrose water preference (%)=(Intakes of sucrose water/[Intakes of sucrose water+Intakes of common sugar-free water])×100

B. Results

Figure 7A:
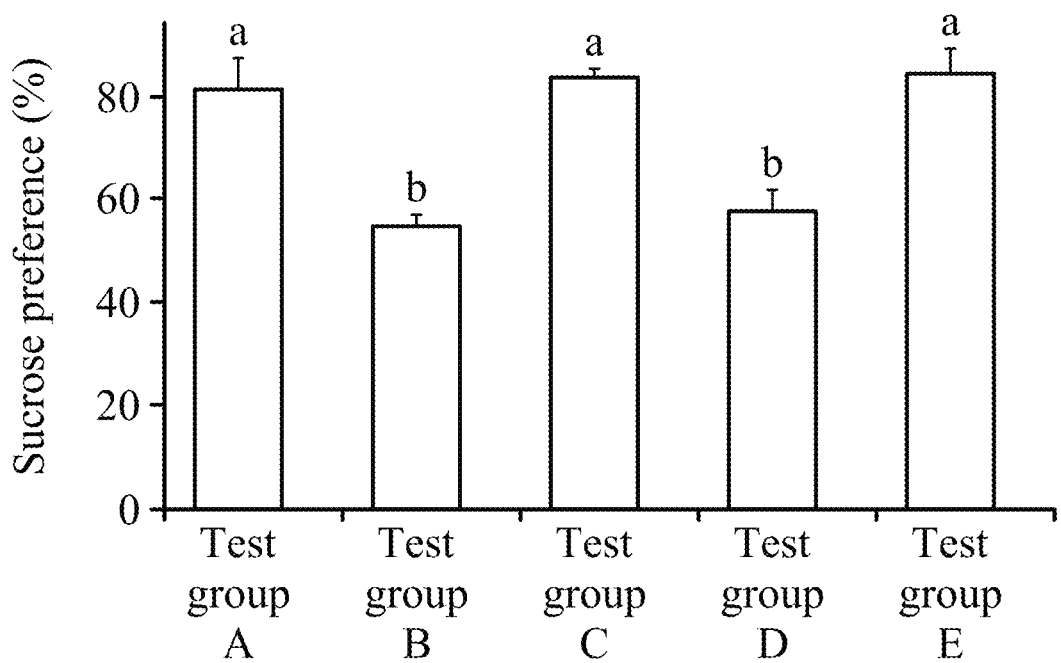
FIGS. 7A and 7B show the results of the sucrose water preference test of one embodiment of the present disclosure.
Figure 7B:
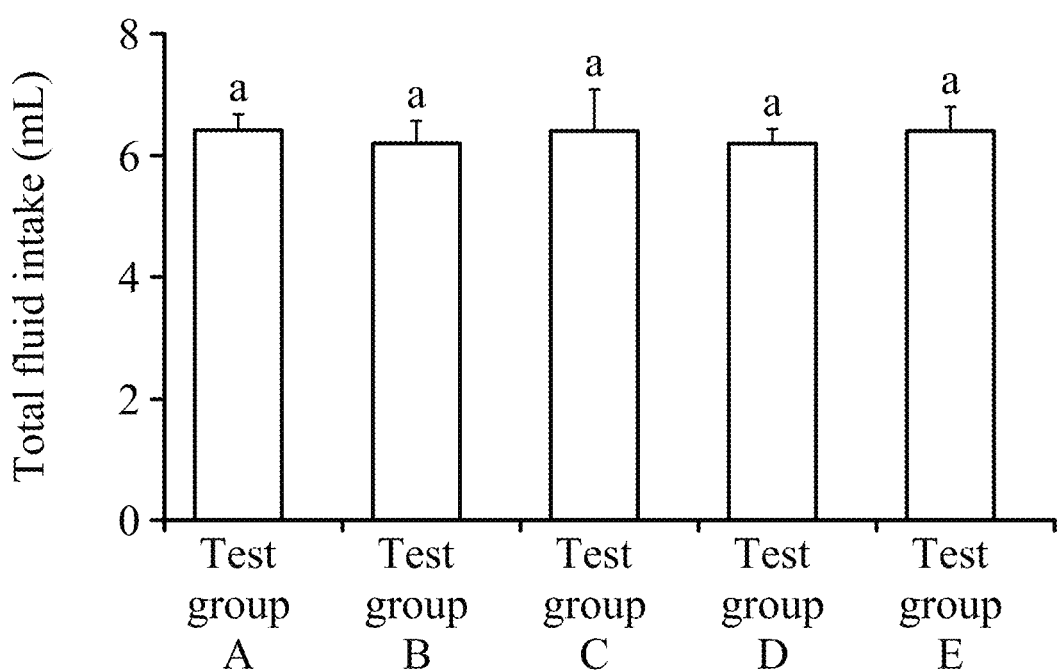

The results of sucrose water preference test are shown in FIGS. 7A and 7B. FIG. 7A shows the sucrose water preference of the mice while FIG. 7B shows the total fluid intake of the mice.

Based on the experimental results shown in FIG. 7A, it is known that, compared to the mice of the blank group (Test group A), sucrose water does not attract mice only induced by corticosterone (Test group B) to drink.

The above results show that mice with depression-like/anxiety-like symptoms are less hedonic.

Based on the experimental results shown in FIG. 7A, it is known that, compared to the mice only induced by corticosterone (Test group B), the sucrose water preference for the mice orally administered with lactic acid bacteria (Test group C) or the ferment of the water extract of *Gracilaria blodgettii* formed by the lactic acid bacteria (Test group E) are significantly increased (p<0.05). However, oral administration of the water extract of *Gracilaria blodgettii* (Test group D) cannot raise the sucrose water preference for the mice. In addition, FIG. 7B shows that there is no significant difference in the total fluid intake between the groups, and this means that the improvement effect of the lactic acid bacteria and the ferment of the water extract of *Gracilaria blodgettii* formed by the lactic acid bacteria is not due to the difference in the drinking amount of water.

The above results show that *Gracilaria blodgettii* fermented by lactic acid bacteria can promote hedonic behavior of mice and has a good effect on improving emotional response.

Example 6

Effects of Water Extract of *Gracilaria blodgettii* and Ferment Thereof on the Content of Stress Hormones in Serum A. Methods The mice of each group of Example 3 were used to perform this experiment.

14 days after starting to feed the feed sample, blood was collected from the mice to determine the concentration of the serum corticosterone and adrenaline in the mice.

Both corticosterone and adrenaline are stress response related hormones, and their high blood concentration in the organism can cause depression/anxiety in animals.

B. Results

Figure 8A:
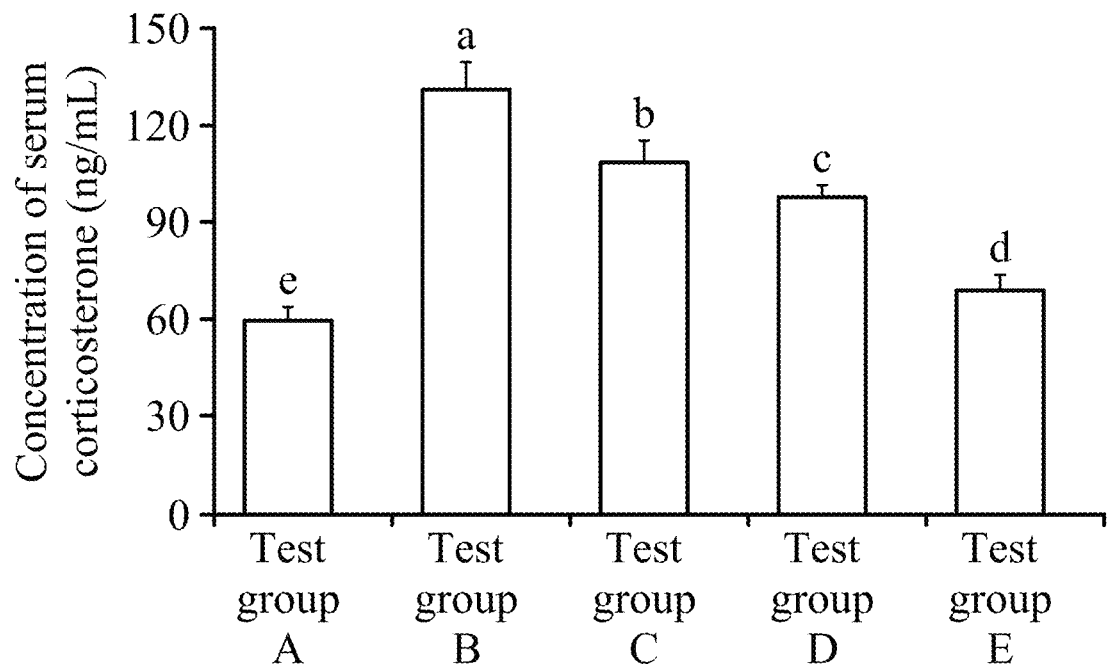
FIGS. 8A and 8B show the results of stress hormone determination in mouse serum of one embodiment of the present disclosure.
Figure 8B:
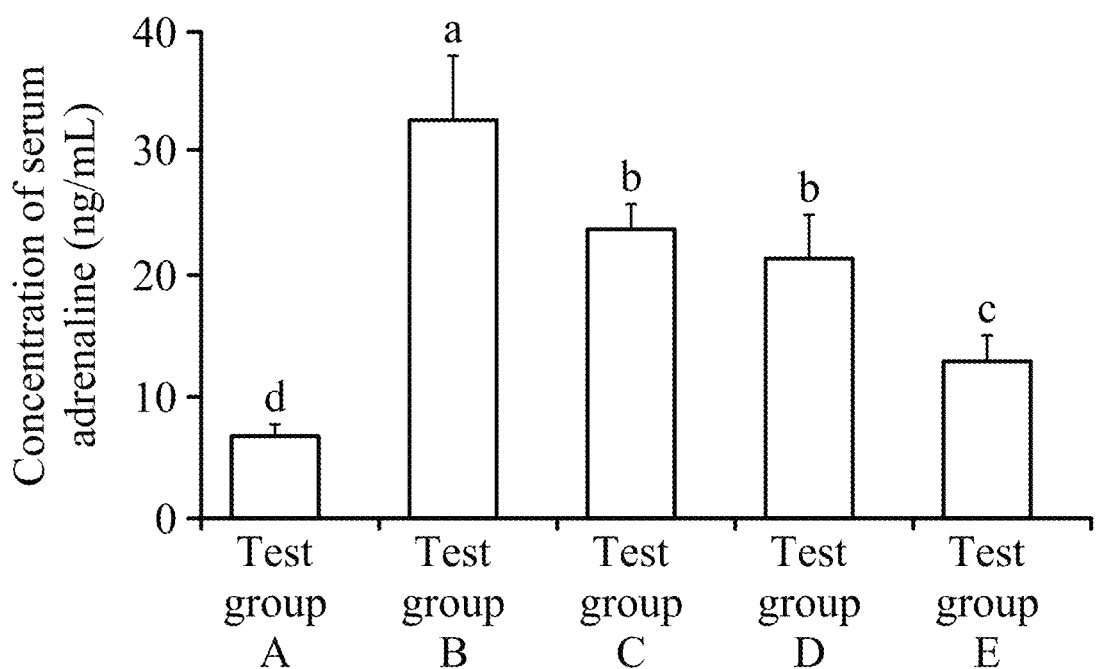

The results of hormone determination in serum are shown in FIGS. 8A and 8B. FIG. 8A shows the corticosterone concentration in serum of the mice while FIG. 8B shows the adrenaline concentration in serum of the mice.

FIGS. 8A and 8B show that, compared to the mice of the blank group (Test group A), after the mice are induced by corticosterone (Test group B), serum concentrations of stress hormones, corticosterone and adrenaline, significantly increase (p<0.05).

Furthermore, FIGS. 8A and 8B also show that oral administration of lactic acid bacteria (Test group C), the water extract of *Gracilaria blodgettii* (Test group D) or the ferment of the water extract of *Gracilaria blodgettii* formed by the lactic acid bacteria (Test group E) can significantly inhibit stress hormone contents in the mice raised by corticosterone induction (p<0.05). In addition, the effects of inhibiting stress hormones in serum of the ferment of the water extract of *Gracilaria blodgettii* formed by the lactic acid bacteria are significantly better than those of the lactic acid bacteria and the water extract of *Gracilaria blodgettii* (p<0.05).

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. A method for treating and/or alleviating nervous diseases, comprising:
    administering an effective amount of a water extract of a plant belonging to the family Gracilariaceae or a ferment of the water extract of a plant belonging to the family Gracilariaceae to a subject in need thereof to treat and/or alleviate a nervous disease of the subject,
    wherein the ferment of the water extract of a plant belonging to the family Gracilariaceae is a ferment formed by a lactic acid bacterium, and
    wherein the plant belonging to the family Gracilariaceae comprises *Gracilaria blodgettii*, *Gracilaria coforvoides*, *Gracilaria gigas*, *Gracilaria chorda*, *Gracilaria lichenoides* or *Gracilaria compressa*, and wherein the lactic acid bacterium is a bacterium belonging to the genus *Lactobacillus* and the bacterium belonging to the genus *Lactobacillus* comprises *Lactobacillus plantarum, Lactobacillus acidophilus, Lactobacillus bulgaricusk* or *Lactobacillus gasseri*, and wherein the nervous disease is depression, bipolar disorder or anxiety.

2. The method for treating and/or alleviating nervous diseases as claimed in claim 1, wherein the water extract of a plant belonging to the family Gracilariaceae is obtained in the following step:

performing a procedure of heating under reflux on a plant belonging to the family Gracilariaceae with water to obtain a water extract in the form of extract solution; or performing a procedure of heating under reflux on a plant belonging to the family Gracilariaceae with water to obtain a water extract solution and drying the water extract solution to obtain a water extract in the form of extract powder.

3. The method for treating and/or alleviating nervous diseases as claimed in claim 2, wherein the weight ratio of the plant belonging to the family Gracilariaceae to the water is about 1:5-100.

4. The method for treating and/or alleviating nervous diseases as claimed in claim 1, wherein the ferment of the water extract of a plant belonging to the family Gracilariaceae is formed using a method comprising the following steps:

(a) adding an activated lactic acid bacterium to an aqueous solution, wherein the aqueous solution contains the water extract of a plant belonging to the family Gracilariaceae in the form of extract solution, or the aqueous solution is formed by adding the water extract of a plant belonging to the family Gracilariaceae in the form of extract powder to water; and (b) performing a fermentation procedure on the aqueous solution to form the ferment of the water extract of a plant belonging to the family Gracilariaceae.

5. The method for treating and/or alleviating nervous diseases as claimed in claim 4, wherein in the aqueous solution, the content of the extract powder is 1-20% (w/v).

6. The method for treating and/or alleviating nervous diseases as claimed in claim 4, wherein in step (a), the aqueous solution consists of the extract solution or the aqueous solution is only formed by adding the extract powder to water.

7. The method for treating and/or alleviating nervous diseases as claimed in claim 6, wherein in the aqueous solution, the content of the extract powder is about 10% (w/v).

8. The method for treating and/or alleviating nervous diseases as claimed in claim 4, wherein in step (a), the aqueous solution further comprises a saccharide.

\* \* \* \* \*